United States Patent [19]

Takahashi

[11] 4,053,756

[45] Oct. 11, 1977

[54] ILLUMINATION LIGHT-SOURCE DEVICE FOR AN ENDOSCOPE OR THE LIKE

[76] Inventor: Nagashige Takahashi, No. 4-1, Nishi, Kokubunji, Tokyo, Japan

[21] Appl. No.: 644,781

[22] Filed: Dec. 23, 1975

[30] Foreign Application Priority Data

Dec. 26, 1974   Japan ............................. 50-3926[U]

[51] Int. Cl.$^2$ ............................................. A61B 1/06
[52] U.S. Cl. ........................................ 362/7; 128/6; 362/32
[58] Field of Search .................. 240/1.3, 2.18, 37.1, 240/41 R, 41.15, 41.3, 41.35, 41.4 R, 46.49, 46.49 A, 41.35 A, 41.35 B; 354/62, 126, 132; 352/198, 200, 203; 128/6, 7, 8

[56] References Cited
U.S. PATENT DOCUMENTS

| 1,204,823 | 11/1916 | Rueter .................... 240/41 R |
| 2,158,561 | 5/1939 | Biggs .................. 240/46.49 R |
| 2,277,697 | 3/1942 | Grier ....................... 240/1.3 |
| 2,441,823 | 5/1948 | Kurlander ............. 240/46.49 R |
| 2,443,357 | 6/1948 | McMath et al. .............. 240/1.3 |
| 2,482,430 | 9/1949 | Noel ........................ 240/1.3 |
| 2,542,311 | 2/1951 | Carlson ..................... 240/1.3 |
| 2,749,482 | 6/1956 | Fruengel .................. 240/41 R |
| 2,867,209 | 1/1959 | Foures ......................... 128/6 |
| 2,936,753 | 5/1960 | Storz .......................... 128/6 |
| 2,949,071 | 8/1960 | Foures ......................... 128/6 |

FOREIGN PATENT DOCUMENTS

| 593,522 | 5/1925 | France .................... 240/41 R |
| 266,366 | 6/1927 | United Kingdom ...... 240/41 R |

Primary Examiner—L. T. Hix
Assistant Examiner—Alan Mathews
Attorney, Agent, or Firm—Sughrue, Rothwell, Mion, Zinn and Macpeak

[57] ABSTRACT

A light source for an endoscope includes a lamp for providing conventional illumination, a cold mirror for condensing the conventional illumination onto a light incident surface of a light guide, and a flash discharge tube or lamp for providing flash illumination for photography. The conventional lamp has a sealed tip portion which is adjacent a reflective coating on a part of the outer periphery of the flash discharge tube.

3 Claims, 1 Drawing Figure

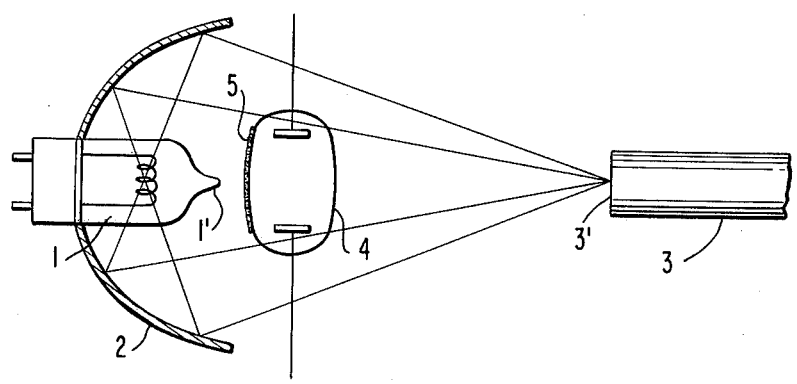

ILLUMINATION LIGHT-SOURCE DEVICE FOR AN ENDOSCOPE OR THE LIKE

BACKGROUND OF THE INVENTION

This invention relates to a light source device, particularly adapted for use in an endoscope used to illuminate the interior of a body cavity.

As is well known, in an endoscope the interior of a body cavity is examined by means of light from a light source passing through a fiber optical system towards the end of said endoscope. As a result it is possible to effect peep-through observation or photography. Often there is provided separate light sources for simple viewing and for photography, respectively. The first being a conventional light source and the latter being a flash light source.

Visual examination of a mucus membrane part to be examined within a body cavity using an endoscope is carried out under the illumination thereof by a conventional lamp such as a tungsten filament lamp, having a relatively low intensity of illumination because of the possibility of damage to the membrane by sustained high intensity light. It is also typical to photograph the desired part after it has been found by simple viewing and adjustment of the endoscope tip. Photographic recording is carried out under the instantaneous illumination at a high intensity by using a xenon discharge tube or the like. Accordingly, the endoscope illumination device must include an observing light source and a photographic light source.

The latter light sources are provided external to the fiber optical system of the endoscope. The fiber optical system usually comprises a small-diameter introducing portion, for entry of an objective lens into a part of the body to be examined, and an operating portion with an eyepiece arranged thereon. However, since the introducing portion is required to be flexible and to have a very small diameter the fiber bundles for transmitting light from the lamps to the object and the fiber bundles for transmitting the image light from the object to the eyepiece must necessarily be constrained so as to permit only a single light path or guide. Therefore, both the conventional light and the photography light must impinge the same entry port of the light guide.

Generally, the light sources are arranged such that a flash discharge tube is arranged in front of a tungsten filament lamp which has a reflector at the back thereof. The disposition of the two lamps is such that the discharge lamp would block a substantial amount of the light from the conventional lamp from entering the light guide, were it not for complicated lens systems or specially designed arrangements typically provided to ameliorate the problem. Such systems and arrangements are not satisfactory because of their complexity.

SUMMARY OF THE INVENTION

It is therefore an object of the present invention to provide a simple arrangement of the conventional and photography lamps in an endoscope wherein the amount of conventional light blocked by the photography lamp is reduced substantially.

The latter object is accomplished by placing the reflective coating over the photography lamp adjacent the tip of the conventional lamp.

BRIEF DESCRIPTION OF THE DRAWINGS

The only FIGURE is a view of a preferred embodiment of the invention.

DETAILED DESCRIPTION OF THE INVENTION

In the drawing there are shown the elements in the light source housing of an endoscope. These elements comprise; a conventional lamp 1, such as a tungsten halogen lamp, having a sealed projecting tip 1' and a back curved mirror 2 for reflecting light towards the input port 3' of light guide 3, and a flash discharge tube, such as a xenon discharge tube or the like, positioned in front of the conventional lamp 1. (It should be noted that the terms front and rear, as used herein, designate, respectively, the positions towards the input port 3' and the mirror 2.) The rear side of the flash discharge tube is coated with a reflective material between the electrodes thereof to form a light reflecting portion 5. The reflective material may be adhered by a sputtering process or the like to coat an approximately semi-peripheral region of the outer surface of said discharge tube. It should be noted that this reflection portion 5 may also serve as a trigger electrode of the tube 4. The discharge tube 4 is interposed between the lamp 1 and the light incident surface 3' in the vicinity of the tip of the lamp 1 in a state where the treated surface of the reflection portion 5 is positioned opposite said tip.

The lamp 4 is positioned extremely close to the sealed tip 1' of the lamp 1 so that the conventional light rays condensed by the curved mirror towards the input port 3' are only slightly interfered with by the reflective shield 5. It will be appreciated that the conventional light blocked would be increased by moving the lamp 4 forward toward the input port. It will be noted that the light through the tip 1' will be refracted randomly. Thus, the area just surrounding the tip, in a plane perpendicular to the tip axis, will receive the smallest intensity of illumination from the lamp 1. Therefore the reflective shield is positioned in the latter low intensity illumination region, so as to interfere with only a minimum of the conventional light.

It is therefore important that the flash discharge tube 4, particularly the light reflection portion 5 of the device according to the present invention is positioned adjacent the tip in terms of the light distribution characteristic of the abovementioned lamp. This is designed so that the light reflection portion 5 composed of a curued surface has its external surface also serving as a reflection surface for the lamp light so that the resultant reflected light may be re-reflected by the cold mirror into the light condensed surface.

According to the device of the present invention as constructed above, when the membrane part to be examined is observed with the lamp 1 lighted, the quantity of light from the lamp 1 is scarcely affected by the flash discharge tube 4 positioned frontwardly of the light path of said light, but guided by the light guide 3 to efficiently illuminate the mucus membrane to be examined. Thus, a lamp with a minimal quantity of light may be used to obtain the quantity of light necessary for the illumination as described so that a relatively small type of a light-source cooling mechanism to be associated therewith may be used.

On the other hand, for photography, the flash discharge tube 4 radiates light towards the light incident surface 3' of the light guide 3 by means of the light condensing action of the light reflection portion 5.

Thus, the present invention provides a device wherein a reflection portion is provided on a part of the outer peripheral surface of a flash discharge tube, said reflection portion being simply arranged in the vicinity of the tip of a lamp, whereby the light distribution characteristic of said lamp and the quantity of illuminating light are scarcely affected, whereby loss of light from a conventional lamp may be minimized and said lamp may efficiently be used. Furthermore, the present invention has significant practical advantages such that the quantity of radiation from the flash discharge tube may effectively be increased by using the aforesaid reflection portion as a condenser for condensing the flash discharge ray onto the light incident input of the light guide. The illumination device may be inexpensively constructed because a specially designed condenser lens or the like need not be used for the conventional lamp and a cooling mechanism or the like can be of the simple type.

What is claimed is:

1. A light source for an endoscope or the like for producing viewing light and photographing light and for directing said light to a light incident surface of a light guide, said light source comprising, a first lamp for producing conventional viewing illumination, said lamp having a sealed tip portion pointing in the light path direction towards the said light incident surface, a curved mirror positioned in back of said first lamp for condensing the light from said first lamp onto said light incident surface, a flash discharge tube having a pair of electrodes and a housing, a reflective coating on a semicircular portion of said housing to condense the light from said flash discharge tube, said flash discharge tube being positioned to place the outer surface of said reflective coating just in front of said tip to provide minimum interference with said condensed light from said curved mirror and to direct said condensed flash light from the internal surface of said coated reflector onto said light incident surface.

2. The light source of claim 1 wherein said first lamp is a tungsten halogen lamp.

3. The light source of claim 1 wherein said discharge tube is a xenon discharge tube.

* * * * *